United States Patent [19]

Karlsson et al.

[11] Patent Number: 4,724,205
[45] Date of Patent: Feb. 9, 1988

[54] DIAGNOSIS OF *SHIGELLA DYSENTERIAE*

[76] Inventors: Karl-Anders Karlsson, Nilssons Berg 37, S-411 43 Göteborg; Alf A. Lindberg, Johan Baners väg 46, S-182 75 Stocksund, both of Sweden

[21] Appl. No.: 630,576

[22] Filed: Jul. 13, 1984

[30] Foreign Application Priority Data

Jul. 15, 1983 [SE] Sweden .............................. 8304007

[51] Int. Cl.$^4$ .............................................. C12Q 1/10
[52] U.S. Cl. .......................................... 435/38; 435/4; 435/34; 435/803; 436/501; 536/1.1; 536/53; 536/123
[58] Field of Search ................... 536/1.1, 53, 123; 435/4, 803, 34; 436/501

[56] References Cited

U.S. PATENT DOCUMENTS 3,600,378 8/1971 Marsh et al. ........................ 435/803
3,891,508 6/1975 Merrick .............................. 435/803

OTHER PUBLICATIONS

Chemical Abstracts 77: 29859n.
Chemical Abstracts 90: 121907t.
Chemical Abstracts 93: 198591e.
*Microbiology Including Immunology and Molecular Genetics*, Davis, B. D. et al. (eds), third edition, Harper and Row Publishers, 1980, pp. 646-665.
Brown, J. E. et al., "Inhibition of Protein Synthesis in Intact HeLa Cells by *Shigella dysenteriae* 1 Toxin", *Infection and Immunity*, Jul., 1980, pp. 98-107.
Brown, J. E. et al., "Purification and Biological Characterization of Shiga Toxin from *Shigella dysenteriae* 1", *Infection and Immunity*, Jun., 1982, pp. 99-1005.
Olsnes, S. et al., "Isolation and Characterization of Shigella shigae Cytotoxin", *The Journal of Biological Chemistry*, vol. 255, No. 1, Jan., 1980, pp. 284-289.

*Primary Examiner*—Robert J. Warden
*Assistant Examiner*—Stephen C. Wieder
*Attorney, Agent, or Firm*—Burns, Doane, Swecker & Mathis

[57] ABSTRACT

A composition for therapeutic or diagnostic use in connection with the toxine of *Shigella dysenteriae*. As an active constituent the composition contains or consists of a compound having the formula (I):

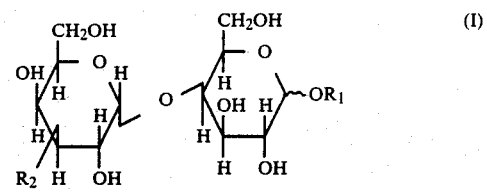

wherein $R_1$ is hydrogen or an organic residue, and $R_2$ is hydrogen, alkyl, alkoxi or a carbohydric residue with the proviso that $R_2$ is not $\beta$-D-GalNacp-(1-0) when $R_1$ is D-Glc or -$\beta$-D-Glcp-(1-0)-ceramide and that $R_2$ is different from OH, α-D-GalNAcp-(1-3)-β-D-GalNAcp-(1-0)-,
β-D-GalNAcp-(1-3)-β-D-GalNAcp-(-0)-,
α-L-Fucp-(1-2)-β-D-Galp-(1-3)-β-D-GalNAcp-(1-0)- and
α-L-Fucp-(1-2)-α-D-Galp-(1-3)-(1-0)-;

a method for therapeutic treatment; and the use of the composition for therapeutic treatment or diagnosis.

7 Claims, No Drawings

DIAGNOSIS OF SHIGELLA DYSENTERIAE

The present invention relates to compounds and compositions which are useful for therapeutic treatment tute the residue of a natural or synthetic glycoconjugate, the compound according to the invention thus being a glycoconjugate, for example a glycolipid.

Moreover, $R_1$ in formula I may be a macromolecular carrier, optionally including a coupling arm. Such carrier can by a synthetically or naturally occurring polypeptide, polysaccharide or other type of polymer or particle.

The invention will in the following be further described in connection with non-limiting examples.

In connection with the creation of the invention a new analysis method has been devised which can be defined as a form of chromatographic binding assay. The principle for same is the following.

A thin layer chromatogram is prepared from pure defined receptor structures and/or receptor structures in a partly unknown mixture extracted from tissue of interest. The thin layer chromatogram is prepared on a surface of silica gel and is treated after the application for avoiding unspecific binding of the substance of interest with a silica gel. The toxin which has been radioactively labelled with $I^{125}$ is then transferred to the treated chromatogram. After washing away excess material, autoradiography indicates which substance remains bound to the individual separated receptor structures. In this manner there information is obtained which indicates which structures are active receptors in relation to the applied toxin and which structures do not show a binding capacity.

The foregoing description of the binding specificity may hereby be obtained by comparision of closely related structures. The identity for a receptor (binding substance) is suitably obtained by comparison with structurally known reference substances. The receptor structures utilized in this disclosure are known substances.

EXAMPLES

The experiment was carried out with a thin layer chromatogram on a surface of silica gel prepared as indicated above. The thin layer chromatogram was detected with anisaldehyde, and autoradiogram was performed after binding with Shigella-toxine labeled with the radioactive iodoisotope $I^{125}$.

The results of the toxin binding studies while using a number of carbohydrate structures are given below in the table, a plus indicating active binding capacity, and a minus indicating lack of binding capacity in relation to the toxin. The table also gives the specificity concerning the binding capacity of the structures according to this invention in that already small deviations in the structure from that defined by formula I results in absence of binding.

TABLE

| Glycolipid | Receptor |
|---|---|
| β-D-Galp-(1-3)-β-D-GalNAcp-(1-3)-α-D-Galp-(1-4)-β-D-Galp-(1-4)-β-D-Glcp-(1-0)-ceramide; | + |
| α-D-Galp-(1-3)-α-D-Galp-(1-4)-β-D-Galp-(1-4)-β-D-Glcp-(1-0)-ceramide; | + |
| Galα1 → 3Galβ1 → 4GlcCer; | − |
| β-D-GalNAcp-(1-3)-α-D-Galp-(1-4)-β-D-Galp-(1-4)-D-Glucitol; | + |
| GalNAcβ1 → 3Galα1 → 3Galβ1 → 4GlcCer; | − |
| GalNAcα1 → 3GalNAcβ1 → 3Galα1 → 4Galβ1 → 4GlcCer; | − |
| Fucα1 → 2Galβ1 → 3GalNAcβ1 → 3Galα1 → 4Galβ1 → 4GlcCer; | − |
| GalNAcβ1 → 3GalNAcβ1 → 3Galα1 → 4Galβ1 → 4GlcCer. | − |

We claim:

1. A method for diagnosing the presence of the toxin of *Shigella dysenteriae* comprising exposing the toxin of *Shigella dysenteriae* to a compound of the formula (I):

(I)

wherein $R_1$ is selected from the group consisting of hydrogen, lower alkyl, lower acyl, natural glycoconjugates, synthetic glycoconjugates, polypeptides, polysaccharides and polymers, and $R_2$ is hydrogen, alkyl, alkoxy or a carbohydric residue with the proviso that $R_2$ is not β-D-GalNacp-(1-O) when $R_1$ is D-Glc or β-D-Glcp-(1-O)-ceramide and that $R_2$ is different from OH,
α-D-GalNAcp-(1-3)-β-D-GalNAcp-(1-O)-,
β-D-GalNAcp-(1-3)-β-D-GalNAcp-(1-O)-,
α-L-Fucp-(1-2)-β-D-Galp-(1-3)-β-D-GalNAcp-(1-O)-,
α-L-Fucp-(1-2)-α-D-Galp-(1-3)-(1-O)-,
and detecting the presence of binding of the toxin of *Shigella dysenteriae* with the compound of formula (I) which is diagnostic for the presence of said toxin.

2. The method according to claim 1, wherein $OR_1$ in formula (I) is in β-configuration.

3. The method according to claim 1, wherein $R_1$ is a carbohydrate residue.

4. The method according to claim 1, wherein $R_2$ is lower alkoxy.

5. The method according to claim 11, wherein $R_1$ is lower alkyl.

6. The method according to claim 1, wherein the compound of formula (I) is present in combination with a pharmaceutically acceptable carrier.

7. A method for determining the presence of the toxin of *Shigella dysenteriae* in a sample from a mammalian organism comprising exposing the sample to a compound of the formula (I):

(I)

wherein $R_1$ is selected from the group consisting of hydrogen, lower alkyl, lower acyl, natural glycoconjugates, synthetic glycoconjugates, polypeptides, polysaccharides and polymers, and $R_2$ is hydrogen, alkyl, alkoxy or a carbohydric residue with the proviso that $R_2$ is not β-D-GalNacp-(1-O) when $R_1$ is D-Glc or β-D-Glcp-(1-O) -ceramide and that $R_2$ is different from OH,
α-D-GalNAcp-(1-3)-β-D-GalNAcp-(1-O)-,
β-D-GalNAcp-(1-3)-β-D-GalNAcp-(1-O)-,
α-L-Fucp-(1-2)-β-D-Galp-(1-3)-β-D-GalNAcp-(1-O)-,
α-L-Fucp-(1-2)-α-D-Galp-(1-3)-(1-O)-,
and determining the degree of interaction between the toxin of *Shigella dysenteriae* contained in the sample and the compound of the formula (I) the degree of interaction indicating the presence of said toxin.

* * * * *